(12) United States Patent
Beichmann et al.

(10) Patent No.: US 7,008,787 B2
(45) Date of Patent: Mar. 7, 2006

(54) CHAMBER FOR THE TREATING CELLS CONTAINED IN A SUSPENSION IN AN ELECTRIC FIELD

(75) Inventors: Boris V. Beichmann, Hamburg (DE); Olaf Faustmann, Apensen (DE); Kurt Lucas, Hamburg (DE); Christian Taesler, Buxtehude (DE); Nico Gülzow, Hamburg (DE); Wolfgang Lübker, Norderstedt (DE); Hans-Joachim Ricklefs, Bargteheide (DE); Nada Pavlovic, Hamburg (DE)

(73) Assignee: Eppendorf AG, Hamburg (DE)

( * ) Notice: Subject to any disclaimer, the term of this patent is extended or adjusted under 35 U.S.C. 154(b) by 78 days.

(21) Appl. No.: 10/106,937

(22) Filed: Mar. 26, 2002

(65) Prior Publication Data

US 2002/0164776 A1     Nov. 7, 2002

(30) Foreign Application Priority Data

Mar. 27, 2001   (DE) ................................. 101 16 211

(51) Int. Cl.
*C12M 1/42* (2006.01)
(52) U.S. Cl. .............................. 435/285.2; 435/173.6; 204/643
(58) Field of Classification Search ................ 435/450, 435/461, 470, 173.5–173.7, 285.2; 204/242, 204/547, 643
See application file for complete search history.

(56) References Cited

U.S. PATENT DOCUMENTS

| | | | | |
|---|---|---|---|---|
| 4,578,167 A | * | 3/1986 | Schoner ....................... | 435/450 |
| 5,589,047 A | * | 12/1996 | Coster et al. ................ | 204/450 |
| 5,593,565 A | * | 1/1997 | Ajdari et al. ................ | 204/643 |
| 5,993,632 A | * | 11/1999 | Becker et al. ............... | 204/547 |
| 6,492,175 B1 | * | 12/2002 | Muller et al. ................ | 435/450 |
| 2001/0047941 A1 | * | 12/2001 | Washizu et al. ............. | 204/547 |
| 2002/0036141 A1 | * | 3/2002 | Gascoyne et al. .......... | 204/547 |

FOREIGN PATENT DOCUMENTS

| CA | 2238254 A1 | * | 11/1999 |
|---|---|---|---|
| DE | 19500660 A1 | * | 6/1996 |
| DE | 19859459 A1 | * | 6/2000 |

* cited by examiner

*Primary Examiner*—William H. Beisner
(74) *Attorney, Agent, or Firm*—Abelman, Frayne & Schwab

(57) ABSTRACT

A chamber for treating cells contained in a suspension in an electric field, the chamber having a vessel for holding the suspension and at least two electrodes with electrode surfaces that face each other. The suspension may be placed between the electrode surfaces and the electrodes are connectable to different poles of a source of voltage to generate an electric field between the electrode surfaces. The electrodes are laminate and continuous and are configured to generate a non-uniform field. Moreover, the electrodes have electrode surfaces made of electrically conductive material, wherein the electrode surface of at least one of the two electrodes is shaped such that a non-uniform field with several maxima distributed over the electrode surface may be generated between the two electrodes.

8 Claims, 2 Drawing Sheets

CHAMBER FOR THE TREATING CELLS CONTAINED IN A SUSPENSION IN AN ELECTRIC FIELD

BACKGROUND OF THE INVENTION

The invention relates to a chamber for the electrofusion of cells.

As a rule, in electrofusion, two different cells are fused together in an electric field. The term "cells" as employed within this application generally refers to biological cells, and in particular cells consisting of body tissues.

Of particular interest at the present time is, for example, the preparation of fusion products consisting of dendritic cells and tumor cells by electrofusion. Dendritic cells are immunoactive cells that may have antigens on their surfaces and that, as a function of these antigens, exhibit differing immunostimulating properties.

Fusion products from dendritic cells and tumor cells may be employed, for example, in tumor therapy. In this context, the publication by Kugler et al. in Nature Medicine, Volume 6, pages 332 to 336 (2000), describes the use of the above fusion products in the treatment of kidney carcinoma in humans.

Chambers of this type, a.k.a fusion cuvettes, in which the electrofusion of cells may be carried out, typically have a vessel for the suspension containing the cells and at least two electrodes whose electrode surfaces face each other. The electrodes are configured such that there is suspension between the electrode surfaces during operation of the chamber. When the electrodes are connected to different poles of a source of voltage, an electric field is generated between the electrode surfaces and this electric field brings about the electrofusion of the cells contained in the suspension.

The electrofusion can take place in three steps. In a first pre-alignment step, the cells contact each other by dielectrophoresis. In a second pulse step, a pulse is emitted causing the cell membranes to rupture such that cell membranes and, thus, the cells can fuse. To stabilize the fusion partners, in a third post-alignment step, the ruptured cells are kept in contact with each other by dielectrophoresis until the fusion is complete.

The aforementioned step sequence is not the only possible sequence for these steps. It is possible that only the pulse is emitted and then, if necessary a centrifugation step may follow to stabilize the fusion.

A comprehensive description of electrofusion may be found, for example, in the book by U. Zimmermann & G. Neill ("Electro manipulation of cells", CRC Pub., Boca Raton, Fla., United States, 1996).

In electrofusion, the electric field generated in the chamber must be non-uniform. Only in a non-uniform field does the desired alignment of the cells by dielectrophoresis take place in the area of the highest field strength.

Various devices of this type are known in which non-uniform fields are generated. For example, German patent DE 3317415 describes a chamber that has a cylindrical core around which the wire-like electrodes are wound as a double helix. This chamber yields good fusion results. With such devices, however, only small volumes of suspension can be processed that may be insufficient for some applications such as, for example, the above-mentioned cancer therapy.

U.S. Pat. No. 4,578,168 discloses a chamber into which several flat wire mesh electrodes have been inserted. The disadvantage of this structure is that the cells get tangled in the mesh structures of the electrodes and are consequently difficult to remove after the fusion has been completed.

The above-mentioned publication in Nature Medicine, Volume 6 (2000) describes the use of an electroporation cuvette whose electrodes have been coated with a dielectric wax to create the desired non-uniform field. The disadvantage is that such an arrangement does not allow standardization or reproducibility.

SUMMARY OF THE INVENTION

The objective of the invention is to create a chamber, especially for electrofusion, which, in comparison to the state of the art, allows the processing of larger suspension volumes under well-defined conditions.

This objective is achieved with a chamber in accordance with the invention. The invention provides for chambers having laminate, continuous electrodes with electrode surfaces made of electrically conductive material; the electrode surface of at least one of the two electrodes is shaped such that a non-uniform field with several maxima distributed over the electrode surface is generated between the two electrodes.

The invention provides for electrodes having continuous electrode surfaces and electrodes whose electrode surface is only partially present in the areas of the electrode where the desired field strength maxima are to be generated. In this context, for example, an electrode has an insulating core that is partially provided with strip-like coatings consisting of electrically conductive material, wherein said coatings are contacted together.

An important advantage of the invention is that the continuous electrodes of the chamber of the invention, in contrast to the known wire mesh electrodes, may be easily rinsed off. Consequently, in accordance with the invention, the formed fusion products can be removed without any difficulties from the chamber after the electrofusion has been completed.

In an embodiment of the invention, at least one of the electrode surfaces of the two electrodes has elevations that define areas where the distance to the other facing electrode surface is less than the distance in the surrounding areas. In each instance, the field generated between the two electrode surfaces, in the area of these elevations, has maximum values where the cells line themselves up during electrofusion.

These elevations may have any desired shape such as, for example, pyramidal or hemispherical, etc. In another preferred embodiment, the electrode surface has a wavy shape. The desired field strength maxima are formed in these wave peaks and interrupted by lower field strength values in the adjacent wave valleys.

It is possible for the elevations, for example, the waves, to be formed in only one electrode surface while the other electrode surface is flat. Another preferred embodiment of the invention, however, provides for both electrode surfaces facing each other to have elevations that are opposite from each other. Such an embodiment provides well-defined areas with a markedly higher field strength than the field strength in the surrounding areas.

In the embodiment in which the wavy electrode surfaces are provided, the wave peaks and the wave valleys may run in the same direction, in the two electrode surfaces facing each other. It is also possible for the wave peaks and valleys to be positioned at an angle relative to each other. Such positioning results in a larger number of areas with field strength maxima that may be advantageous for some applications.

The surfaces of the electrodes may be partially coated with a non-electrically conductive material and leveled such that only the areas that generate the desired field strength maxima remain free in order to provide good rinsing properties. For example, in the wavy electrode surface embodiment, it is possible to fill up the wave valleys such that the coated electrode surface acquires an approximately flat surface from which the cells or fusion products can be readily rinsed off.

The electrodes may be made completely of an electrically conductive material. It is also possible, however, for the electrodes to have a core made of a different material and for only the electrode surface to be applied onto this core as a coating consisting of conductive material. The electrode surface, in turn, can then, as mentioned above, be provided with another partial coating made of material that is not electrically conductive.

Particularly, for the embodiment wherein the electrode surface is applied onto the core as a coating consisting of conductive material, the electrode surface may be only partially present on the electrode. For this embodiment, the electric power needed is less than the power needed for the embodiment where the electrode surface is continuous, and the advantageous rinsing properties is retained.

The selection of suitable electrically conductive materials is not limited. Any material may be used that can be appropriately processed and with which the fields necessary for electrofusion may be generated.

Preferably, electrically conductive plastics (carbon-filled plastics) or semiconductor materials may be used to simplify the process. These materials may be processed easily by the injection-molding technique, which is advantageous for chambers that are disposable. It is also possible, however, to use metallized plastic plates.

Like the state of the art, the chamber may include at least two electrodes, whose surfaces face each other, which may be arranged or which may already be permanently placed.

It is also possible, for example, for a large number of parallel electrodes to be arranged inside the chamber and for these electrodes to form pairs of electrodes whose surfaces face each other.

The chamber, in accordance with the invention, may also have a cover to securely close (i.e. liquid-tight) the vessel for the suspension. The electrodes may be attached to the cover and may, for example, then be removed from the chamber to be rinsed. The wiring that connects the electrodes to the power source may similarly be installed in the cover.

Another preferred embodiment provides for the distance of the electrodes relative to each other, in the chamber, to be varied. It is possible, for example, to mount the electrodes in rails, or the like, wherein the electrodes can be slid to the desired electrode distance.

The chamber, in accordance with the invention, may be disposable. Irrespective of whether the chamber is disposable or used repeatedly, the chamber should be made such that it may be sterilized. Preferably, the chamber is designed such that it may be sterilized with the electrodes by irradiation.

As mentioned above, electrofusion may be carried out in several steps during which different electric fields are applied to the suspension containing the cells. It is also similarly possible that only one pulse be emitted to bring about the desired alignment of the cells and, almost simultaneously, the fusion. Instead of an electric field, the cells may also be compacted through the force of gravity, particularly, by centrifugation for stabilizing the fusion products. In this context, another embodiment of the invention provides for the chamber to be designed so that it may be centrifuged.

Finally, a last embodiment is relevant to the suspension volumes to be processed. As discussed above, one objective of the invention is to process the largest possible suspension volumes. In the above-mentioned embodiments, the chamber, in accordance with the invention, already allows suspension volumes to be processed that are sufficient for the applications currently envisaged. If even larger volumes are to be processed, another embodiment of the invention provides for the chamber to be designed as a flow-through chamber. In this embodiment, the chamber has a connection for a feed line and a connection for a discharge line and, if applicable, liquid-conveying means inside the chamber to allow flow-through operation.

BRIEF DESCRIPTION OF THE DRAWINGS

The invention will be explained in greater detail below with reference to the drawings showing two exemplary embodiments, wherein.

DETAILED DESCRIPTION OF THE INVENTION

Figure 1:
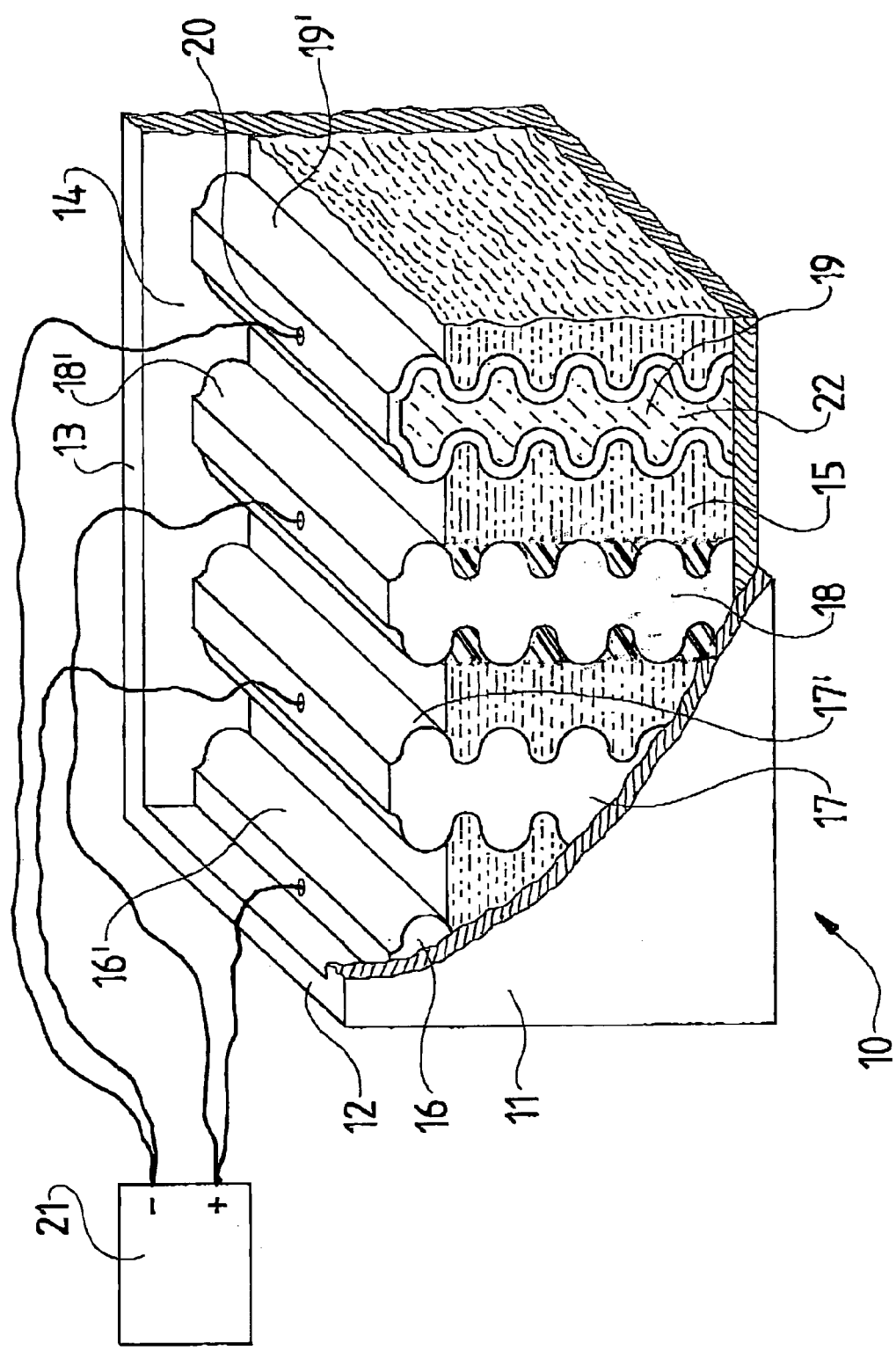
FIG. 1—shows a partial view of an embodiment of the chamber according to the invention.

FIG. 1 shows a partial view of a chamber 10 having walls 11, 12 and 13 that form an inner vessel 14, which is filled with the suspension 15 containing the cells.

Not shown in FIG. 1 is a cover that can be used to close chamber 10.

Electrodes 16, 17, 18 and 19 are provided inside chamber 10. The shown electrodes have wavy electrode surfaces 16', 17', 18' and 19', whereby there are electrode surfaces on both sides of each of the electrodes 17, 18 and 19.

As shown, for example, in electrode 19, the electrodes have contact points 20 to connect the electrodes to a pole of a source of voltage 21.

The electrodes 16, 17 and 18 shown in FIG. 1 consist entirely of a conductive material. Electrode 19, in contrast, has a core 22 onto which electrode surfaces 19' are provided as a coating made of conductive material.

It is also possible to leave out the core 22 and for electrode 19 to only have the electrode surfaces 19'.

In the embodiment shown in FIG. 1, the electrodes are wired pair-wise, in other words, electrodes 16 and 18 are connected to one pole of the source of voltage 21 while electrodes 17 and 19 are connected to the other pole of the source of voltage 21.

The embodiment shown in FIG. 1 allows an exemplary simple realization of the invention.

Other embodiments are, of course, also feasible. Thus, for example, in an alternate embodiment only one of the electrode surfaces may be wavy while the other of the electrode surfaces is flat. It is also possible for the wavy electrode surfaces not to be oriented in the same direction but rather to be oriented at differing angles.

Figure 2:
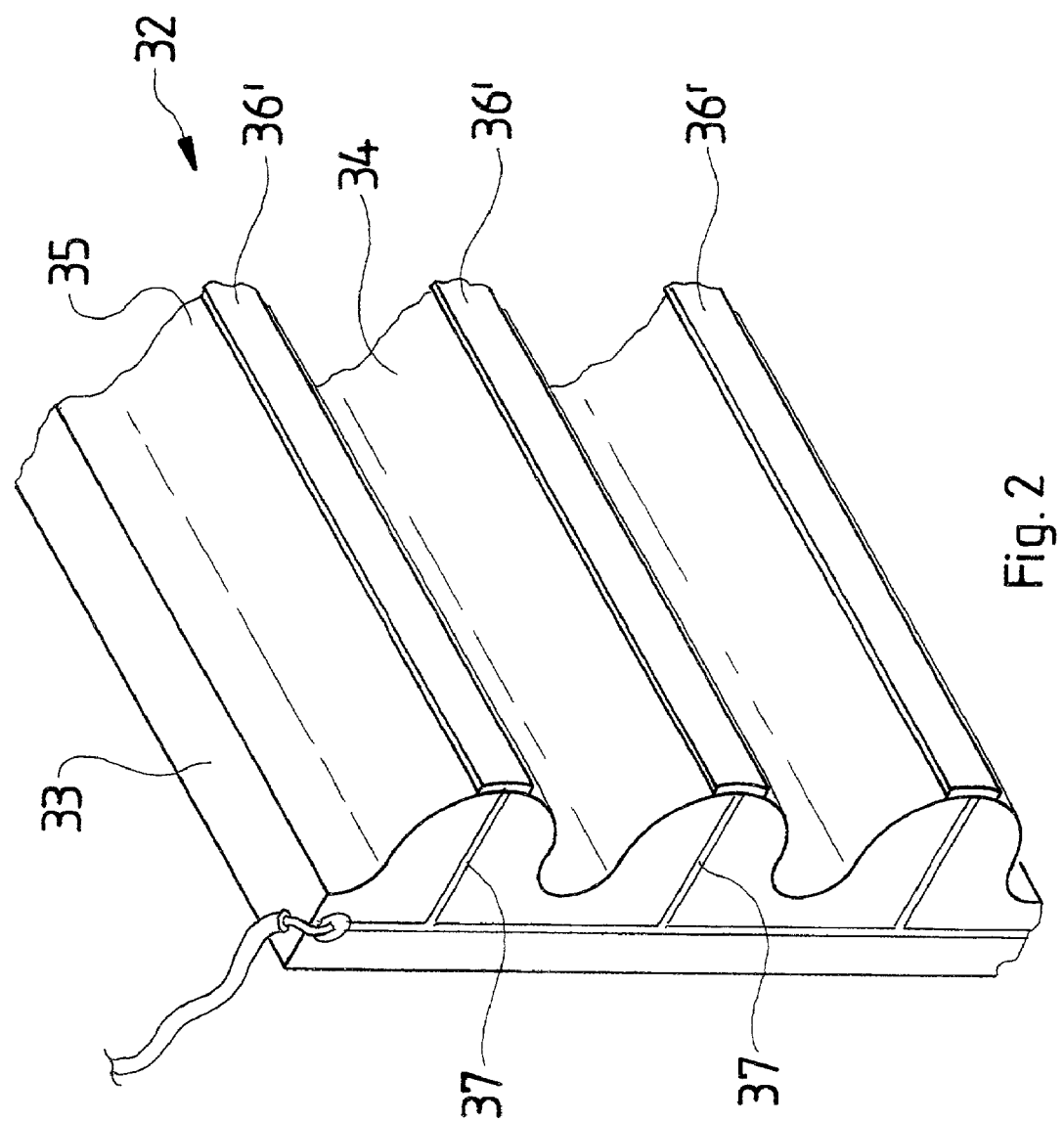
FIG. 2—shows another embodiment with an electrode that may be employed in the chamber according to the invention.

FIG. 2 shows an electrode 32 having a core 33 made of insulating material. The core 33 has a wavy surface 34 with wave peaks 35. On the surface 34, there is an electrode surface including partial coatings 36' of the wave peaks 35. Therefore, the surface 34 is not electrically conductive between the wave peaks 35. The electrode surface or its coatings 36' that are partially formed on the surface 34 may be connected, via lateral connections 37, to one pole of a source of voltage not shown here.

The advantage of an electrode of the embodiment shown in FIG. 2 is that a non-uniform field with defined maxima may be generated, whereby a weaker current may be applied than the current that would be necessary for a continuous electrode surface.

It is also possible to provide such partial coatings on an electrode with a core having a flat surface. In such a case, as well, defined field strength maxima could be generated.

What is claimed is:

1. A chamber for treating cells in a suspension in an electric field, the chamber comprising a vessel in which the suspension may be placed and at least two electrode surfaces face each other, wherein the suspension is between the electrode surfaces and the electrodes are connectable to different poles of a source of voltage to generate an electric field between the electrode surfaces, and the electrodes are configured such that a non-uniform field is generated, wherein the electrodes (16, 17, 18 and 19) are laminate and continuous and have electrically conductive electrode surfaces (16', 17' 18', 19'), wherein an electrode surface (16', 17' 18', 19', 36') of at least one of two electrodes (16', 17' 18', 19', 32) is shaped such that a non-uniform field with several maxima distributed over the electrode surface is generated between the two electrodes (16', 17' 18', 19', 32); wherein the electrode surfaces (16', 17' 18', 19') are continuous, wherein the electrode surface has elevations in several areas, wherein the electrode surface (16', 17' 18', 19', 36') has a wavy shape, wherein facing electrode surfaces of the two electrodes are wavy and include wave peaks and wave valleys that are oriented in the same direction and that lie opposite each other, in both surfaces, and wherein the wave valleys are filled with an insulating material.

2. The chamber of claim 1, further comprising a cover to close the vessel (14).

3. The chamber of claim 2, wherein at least some of the electrodes are arranged on the cover.

4. The chamber of claim 1, wherein the electrode surfaces are made of electrically conductive plastic or of semiconductor materials.

5. The chamber of claim 1, wherein the chamber is designed to be sterilized by irradiation.

6. The chamber of claim of claim 1, wherein the chamber is designed to be centrifuged.

7. The chamber of claim 1, further comprising means for feeding the suspension through the chamber in a flow-through mode.

8. The chamber of claim 1, wherein the chamber is a disposable article.

* * * * *